(12) United States Patent
Geisert

(10) Patent No.: US 6,902,537 B1
(45) Date of Patent: Jun. 7, 2005

(54) UPPER BODY SUPPORT DEVICE

(76) Inventor: Christopher P. Geisert, 1033 Beechwood NE., Grand Rapids, MI (US) 49505

( * ) Notice: Subject to any disclaimer, the term of this patent is extended or adjusted under 35 U.S.C. 154(b) by 0 days.

(21) Appl. No.: 10/824,580

(22) Filed: Apr. 14, 2004

(51) Int. Cl.[7] .......................... A61F 13/00; A47C 20/00
(52) U.S. Cl. ............................................. 602/19; 5/632
(58) Field of Search ................... 297/452.35, 230.12, 297/284, 460, 452.29, 452.3, 452.33; 5/630, 632, 633, 636; 602/18, 19, 17; 128/845, 846

(56) References Cited

U.S. PATENT DOCUMENTS

| | | | |
|---|---|---|---|
| 2,351,849 A | 6/1944 | Wells et al. | |
| 3,009,172 A | 11/1961 | Eidam | |
| D202,691 S | 11/1965 | Essman | |
| 3,361,471 A | * 1/1968 | Radford | 297/230.12 |
| 3,648,308 A | 3/1972 | Greenawalt | |
| 4,535,495 A | * 8/1985 | Oldfield | 297/452.32 |
| 5,390,682 A | * 2/1995 | Iams | 5/632 |
| 5,581,831 A | 12/1996 | Xiang | |
| 5,632,050 A | 5/1997 | Zajas et al. | |
| 5,743,271 A | 4/1998 | Royo-Salvador | |
| 5,987,675 A | 11/1999 | Kim | |
| 6,128,797 A | 10/2000 | Shaffer | |
| 6,412,127 B1 | 7/2002 | Cuddy | |
| 2002/0112289 A1 | 8/2002 | Troop | |

* cited by examiner

*Primary Examiner*—Kim M. Lewis
(74) *Attorney, Agent, or Firm*—Price, Heneveld, Cooper, DeWitt & Litton

(57) ABSTRACT

An upper body device includes a thoracic support region comprising a spinal region having a convex arcuate section on an upper surface thereof to properly position a user's shoulders with respect to the users head, cervical and spinal region.

19 Claims, 1 Drawing Sheet

UPPER BODY SUPPORT DEVICE

BACKGROUND OF THE INVENTION

The present invention relates to devices used to prevent, treat or otherwise aid in the relief of back problems. More particularly, the present invention relates to a support device used for the treatment or prevention of back problems.

There are a number of prior art beds, pillows, cushioning devices and platforms for supporting the head and/or body of a person for various therapeutic and recreational purposes. However, these prior art devices are typically designed for entry positioning and supporting the head and neck region of a user and have heretofore not been suitable for positioning the spinal cord and shoulders of a user, especially with respect to the head and neck region. Therefore, among the various types of devices that have been designed to elevate and/or position the head and neck of a user, none address the proper positioning and support of the spinal cord, especially with respect to the shoulder area.

Therefore, there remains a need for a support device which addresses the aforementioned shortcomings of these prior art devices.

SUMMARY OF INVENTION

In the present invention, an upper body support device includes a thoracic support region comprising a spinal region having a convex arcuate section on an upper surface thereof, to properly position a user's shoulders with respect to the users head, cervical and spinal region.

In an aspect of the present invention, the upper body support device comprises a support pad or pillow made from a resilient foam like material having the aforementioned convex arcuately shaped spinal section and is typically utilized when the patient is lying down or otherwise in a prostrate position.

These and other features, advantages and objects of the present invention will be further understood and appreciated by those skilled in the art by reference to the following specification, claims and appended drawings.

DETAILED DESCRIPTION OF AN EMBODIMENT OF THE INVENTION

Figure 1:
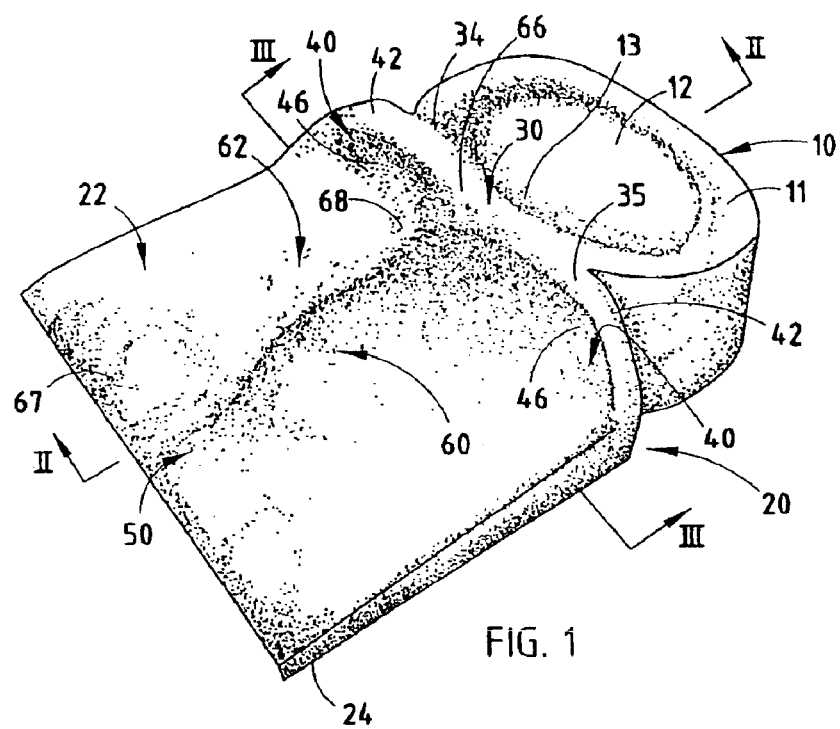
FIG. 1 is a perspective view of the upper body support device embodying the present invention.

In a first embodiment (FIG. 1), the upper body support device 2 includes a first side 22 comprising a head support portion 10 and a thoracic support portion 20, and generally planar second side 24. Thoracic support portion 20 further includes cervical region 30, shoulder region 40, lumbar region 50 and spinal region 60. Further, spinal region 60 includes a convex arcuatcly shaped portion or region 62 which supports a user's spinal area such that the user's head, neck and shoulders are all optimally positioned to prevent and/or treat common back problems as well as promote better sleep.

Head support portion 10 is generally oval in geometry and includes a generally planar surface 11. However, head support 10 may take on various configurations and/or shapes without departing from the inventive concept. In the illustrated embodiment head support 10 and more appropriately planar surface 11 includes a concave surface 12 wherein the users head may be comfortably positioned therein to center and stabilize the occipital region. In the illustrated embodiment, planar surface 11 is generally horizontally disposed when upper body support device 2 is positioned as shown in FIG. 1. Further, planar surface 11 is generally fabricated to be of a height which is equal to cervical region 30. However, planar surface 11 may be fabricated at a height which is above or below cervical region 30 and further, may be fabricated at an angle, as the users specific requirements dictate. Disposed adjacent head support 10 is cervical region 30 of thoracic support portion 20.

Figure 2:
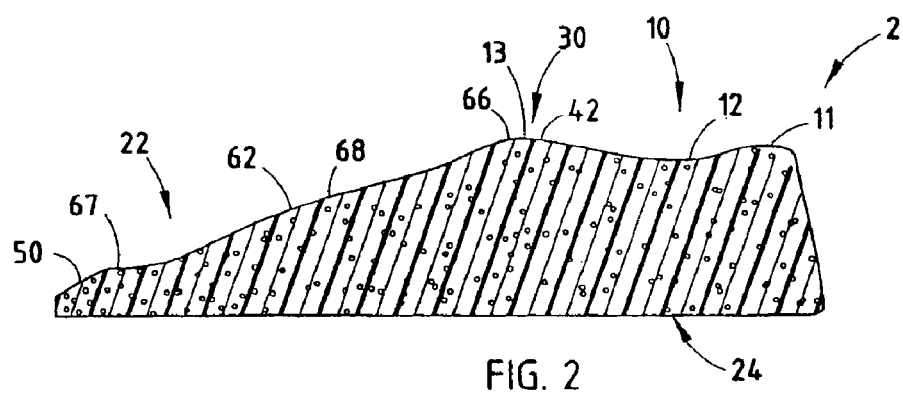
FIG. 2 is a cross sectional view taken along line II—II of FIG. 1.

As best illustrated by FIG. 2, cervical region 30 comprises the area which is generally between head support portion 10 and spinal region 60. In the illustrated embodiment, cervical region 30 is disposed between a peripheral edge portion 13 of concave surface 12 and a first end 66 of spinal region 60. Cervical region 30 supports cervical lordosis while making a smooth transition for the cervicothoracic and cervicalthoracic junctions of the user's body. As discussed previously, cervical region 30 is generally co-plarar with planar surface 11 of head support portion 10. However, cervical region 30 may include a bump, protrusion or other raised surface for increased neck support and/or head tilt. Disposed at opposite lateral ends 34 and 35 of cervical region 30 are blades 42 of shoulder regions 40.

Figure 3:
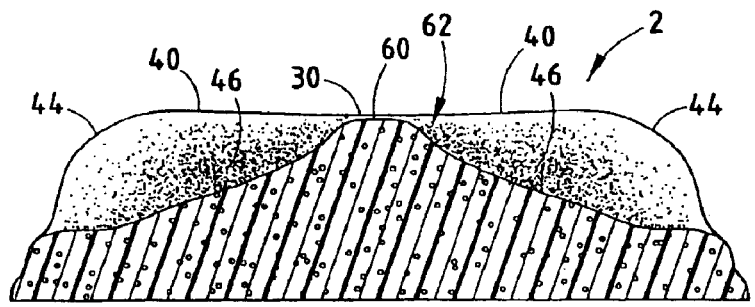
FIG. 3 is a cross section view taken along line III—III of FIG. 1.

Shoulder regions 40 are disposed on opposite sides of spinal region 60. In the illustrated embodiment, shoulder regions 40 include blades 42 which are generally co-planar with cervical region 30 and planar surface 11. Shoulder regions 40 may also include ramped or otherwise non-pointed ends 44 and generally tapered front edges 46 (FIG. 3). Tapered edges 46 are also concave to aid in the support and positioning of the users shoulders. Blades 42 and tapered front edge 46 act to position and retain the user's shoulders thereby ensuring optimal positioning of the patient's shoulder blades with respect to upper body support device 2 and more specifically, spinal region 60.

Disposed between shoulder regions 40 is spinal region 60 which includes a convex arcuately or arched shaped region 62. Spinal region 60 supports cervical lordosis and gently extends the spinal region thereby assisting with normal erect posture. Additionally, convex arcuately shaped region 62 also aides in positioning the shoulders thereby encouraging the stretching of the anterior muscles and tissues and the shortening of the posterior muscles and tissues. In this manner, proper posture is encouraged while simultaneously preventing, treating and/or alleviating back problems.

As best illustrated in FIG. 2, convex arcuately shaped region 62 generally increases in size from second end 67, positioned towards lumbar region 50, and first end 66. That is to say, the convex arcuately shaped region 62 increases in height as well as in width as arcuately shaped region 62 tends from second end 67 toward first end 66. However, convex arcuately shaped region 62 may take on the form of various other geometries. In the illustrated embodiment, convex arcuately shaped region 62 increases in size, as discussed above, from second end 67 to an intermediate point or transition 68. At transition 68, convex arcuately shaped region 62 remains relatively constant in width (as convex arcuately shaped region 62 tends towards first end 66), yet gradually increases in height. In addition to convex arcuately shaped region 62 being tapered, underlying thoracic support portion 20 may also be tapered, as for example from lumbar region 50 towards first end 66 of convex arcuately shaped region 62 thereby adding to the inclination of upper body support device 2 (see FIG. 1). Such a slope creates a transition from the lumbar region and supports the body without interfering with lordosis. In the preferred embodiment, both thoracic support portion 20 and convex arcuately shaped region 62 are tapered such that the tapers increase from lumbar region 50 to first end 66.

In another embodiment, upper body support device 2 includes thoracic support portion 20 but does not include head support portion 10. With this embodiment, a user is free to use an alternative head support, such as for example, a pillow. Therefore, the user will not be restricted to a particular head support but instead may use the support most beneficial to the user's requirements. Alternately, the head may be left unsupported for situations where this is advisable. Further, a separate head support may be supplied with varying heights so that the user can be optimally accommodated. The thoracic support portion 20 of this embodiment is generally as described with regard to the previous embodiment.

Upper body support device 2 may be fabricated from numerous materials. Generally, any material may be used such that a user may be comfortably supported thereon. In the preferred embodiment, a resilient material is used. Such materials are commonly known within the art and may include, but are not limited to, a foam material. Further, head support portion 10 and thoracic support portion 20 may be fabricated from either the same or dissimilar material as the specific requirements dictate. Still further, spinal region 60 may also be fabricated from either the same or dissimilar materials thereby affording the maximum configurability to upper body support device 2. However, in the illustrated embodiment, head support portion 10, thoracic support portion 20 and spinal region 60 are all fabricated from the same resilient foam material. Additionally, the method of fabricating upper body support device 2 is not critical to the inventive concept and support device 2 may be molded, shaped, or made by any other method known in the art. Further, support device 2 may be fabricated from either a single or multiple pieces. However, in the illustrated embodiment support device 2 is molded as a single piece from resilient foam.

As best illustrated by FIG. 1, support device 2 is used by positioning generally planar second side 24 of upper body support device 2 onto a generally planar surface. Such a planar surface may be, for example, a bed, floor or other surface whereon the support device is to be used. Of course, support device 2 is not limited to horizontal surfaces and any generally planar surface can be used and may include chairs, couches or other seating devices. Therefore, support device 2 may be used in either a lying down or seated position. Upper support device 2 may be used to support a user when in a lying down or prostrate position.

Once body support device 2 is positioned on such a surface, the user will then position themselves such that the user's head is supported within concave surface 12 of head support portion 10 while the user's neck is supported by cervical region 30. This positioning ensures that the user's spinal region is positioned over spinal region 60 and more particularly over convex arcuately shaped region 62 while the users shoulders are positioned below blades 42 and residing on or just below tapered edges 46. This positioning optimally places the user's head, neck, shoulder and spinal regions such that the user's head is supported in a generally planar position while the user's neck is comfortably supported by cervical region 30. Further, the convexly arcuately shaped region 62 ensures that the user's spinal region is comfortably supported white tending to elevate the user's spinal cord such that the user's shoulders are biased downwardly by the aforementioned spinal region elevation. This positions the user's thoracic region in a manner which provides for the front chest area of the user to be extended outwardly due to the weight of the user's body, while the user's shoulder areas are biased rearwardly of the front chest area. The resultant positioning of the users thoracic area when using upper body support device 2 can be best described as positioning the user in a "chest out, shoulders back" position thereby providing proper posture and preventing and/or treating various back problems. By utilizing support device 2, the user is correctly positioned, for example while sleeping, while the support device acts to improve the users posture, stretches the users chest muscles and tissue and shortens over-elongated back muscles and tissue caused by poor posture. In addition, support device 2 helps to alleviate snoring by increasing airflow. Further, these benefits are accomplished through the use of a very comfortable support device 2.

The above description is considered that of the preferred embodiments only. Modification of the invention will occur to those skilled in the art and those who make or use the invention. Therefore, it is understood that the embodiments shown in the drawings and described above are merely for illustrative purposes and not intended to limit the scope of the invention, which is defined by the following claims as interpreted according the to principles of patent law, including the doctrine of equivalence.

What is claimed:

1. An upper body support device comprising:

a one-piece structure including a thoracic support portion including a cervical region, a shoulder region, and a spinal region;

said spinal region including a convex arcuate section on an upper surface thereof, and said thoracic support portion including an inclined surface, said inclined surface extending from a lumbar region to said cervical region.

2. The device of claim 1, wherein:

said support device includes a head support portion integral with and adjacent said thoracic portion wherein a person's head may be supported.

3. The device of claim 2, wherein:

said head support portion includes a concave region.

4. The device of claim 1, wherein:

said shoulder region includes a pair of shoulder pads.

5. The device of claim 4, wherein:

said shoulder pads include a tapered front edge and a non-pointed side edge.

6. The device of claim 1, wherein:

said cervical region includes a raised portion.

7. An upper body support device comprising:

a one-piece structure including a thoracic support portion including a cervical region, a shoulder region, and a spinal region;

said spinal region including a convex arcuate section on an upper surface thereof, and said spinal region comprising a taper.

8. The device of claim 7, wherein:

said taper comprises an increased height at said cervical region and decreasing in height to a lumbar region.

9. An upper body support device comprising:

a head support portion;

an inclined thoracic support portion including a cervical region, a shoulder region, a spinal region and a lumbar region, said inclined thoracic support portion disposed adjacent said head support portion;

said spinal region including a convexly arched section on an upper surface thereof.

10. The device of claim 9, wherein:

said inclined thoracic support section is inclined from said lumbar region to said cervical region.

11. The device of claim 9, wherein:

said arched spinal region comprises a taper.

12. The device of claim 11, wherein:

said taper comprises an increased height at said cervical region and decreasing in height to said lumbar region.

13. The device of claim 9, wherein:

said head support portion includes a concave region.

14. The device of claim 9, wherein:

said shoulder region includes a pair of shoulder pads.

15. The device of claim 14, wherein:

said shoulder pads include a concave front edge.

16. The device of claim 9, wherein:

said cervical region includes a raised portion.

17. An upper body support device comprising:

a head support portion comprising a concave region for supporting a person's head;

an inclined thoracic support portion including a cervical region, a shoulder region, a spinal region and a lumbar region, said shoulder region of said thoracic support portion disposed adjacent said head support portion; and said spinal region including a tapered convexly arched section on an upper surface thereof, said taper decreasing in height from said cervical region to said lumbar region.

18. The device of claim 17, wherein:

said inclined thoracic support portion is inclined from said lumbar region to said cervical region.

19. The device of claim 17, wherein:

said shoulder region includes a pair of shoulder pads;

said shoulder pads including a tapered front edge and a non-pointed side edge.

* * * * *

UNITED STATES PATENT AND TRADEMARK OFFICE
CERTIFICATE OF CORRECTION

PATENT NO. : 6,902,537 B1  
DATED : June 7, 2005  
INVENTOR(S) : Christopher P. Geisert It is certified that error appears in the above-identified patent and that said Letters Patent is hereby corrected as shown below:

Title page,
Item [57], ABSTRACT,
Line 1, before "device" insert -- support --.
Line 4, "users" should be -- user's -- (second occurrence).

Column 1,
Line 32, "users" should be -- user's --.
Line 48, "cross sectional" should be -- cross-sectional --.
Line 62, "arcuatcly" should be -- arcuately --.

Column 2,
Lines 5, 13 and 37, "users" should be -- user's --.
Line 24, "co-plarer" should be -- co-planar --.

Column 3,
Line 62, "users" should be -- user's --.

Column 4,
Line 2, "white" should be -- while --.
Lines 9 and 16, "users" should be -- user's --.
Line 30, "equivalence" should be -- equivalents --.

Signed and Sealed this

Sixth Day of December, 2005

JON W. DUDAS  
*Director of the United States Patent and Trademark Office*